(12) United States Patent
Berghofer et al.

(10) Patent No.: US 6,211,400 B1
(45) Date of Patent: Apr. 3, 2001

(54) SULPHINIC ACID DERIVATIVES, METHOD FOR PRODUCING THEM, AND THEIR USE

(75) Inventors: Josef Berghofer, Heilbronn; Harry Rothmann, Daisbach, both of (DE)

(73) Assignee: L. Bruggemann KG (DE)

( * ) Notice: Subject to any disclaimer, the term of this patent is extended or adjusted under 35 U.S.C. 154(b) by 0 days.

(21) Appl. No.: 09/319,108

(22) PCT Filed: Jul. 1, 1998

(86) PCT No.: PCT/EP98/04055

§ 371 Date: May 27, 1999

§ 102(e) Date: May 27, 1999

(87) PCT Pub. No.: WO99/18067

PCT Pub. Date: Apr. 15, 1999

(30) Foreign Application Priority Data

Oct. 2, 1997 (DE) .............................. 197 43 759

(51) Int. Cl.⁷ .................................. C07C 313/02
(52) U.S. Cl. ............................. 560/150; 562/125
(58) Field of Search .................. 560/125, 150; 562/125

(56) References Cited

FOREIGN PATENT DOCUMENTS

| | | |
|---|---|---|
| 841 912 | 6/1952 | (DE) . |
| 1 129 477 | 5/1962 | (DE) . |
| 1 195 742 | 7/1965 | (DE) . |
| 1 643 667 | 6/1971 | (DE) . |
| 27 45 274 | 4/1978 | (DE) . |
| 34 01 500 | 7/1985 | (DE) . |
| 12 40 035 | 5/1994 | (DE) . |
| 195 10 278 | 9/1995 | (DE) . |
| 196 10 745 | 9/1997 | (DE) . |
| 758 150 | 10/1956 | (GB) . |
| 3-85108 | * 4/1991 | (JP) . |
| WO 99/14249 | 3/1999 | (WO) . |

OTHER PUBLICATIONS

M. Mulliez, et al.: "Synthesis of Alpha–Hydroxysulfinates", *Tetrahedron* vol. 49, No. 12, Mar. 1993, pp. 2469–2476, Oxford, GB.

Patent Abstracts of Japan, JP 60/049,068 Mar. 18, 1985.

J.R. Nooi, et al.: "Reactions of Photoexcited $SO_2$: Preparation of Alpha–Substituted Alkanesulphinic Acids", *Tetrahedron Letters*, No. 29, Jun. 1970, pp. 2531–2534, Oxford, GB.

Chemical Abstracts, vol. 96, No. 8, Feb. 22, 1982 96 54156f.

* cited by examiner

*Primary Examiner*—John Hardee
(74) *Attorney, Agent, or Firm*—McDonnell Boehnen Hulbert & Berghoff

(57) ABSTRACT

The present invention relates to sulfinic acid compounds of the formula (I)

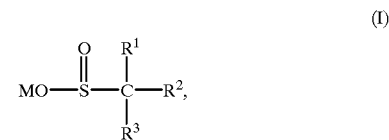

where the substituents are as defined in the description.

The novel sulfinic acid compounds can be used as reducing agents which do not eliminate formaldehyde.

15 Claims, No Drawings

SULPHINIC ACID DERIVATIVES, METHOD FOR PRODUCING THEM, AND THEIR USE

The invention relates to sulfinic acid derivatives and their preparation and use in various application areas.

As is known, sulfinic acid, $H_2SO_2$, is one of the strongest known reducing agents. The free sulfinic acid is unstable. Accordingly, it is only available commercially in the form of its stable and correspondingly manageable derivatives.

The following sulfinic acid derivatives have to date achieved economic importance:

1. Sodium dithionite (fiber bleaching in papermaking, vat dyeing and textile bleaching, mineral bleaching, heavy metal reduction in industrial wastewaters)
2. Sodium formaldehyde sulfoxylate dihydrate (textile discharge printing, textile bleaching, redox cocatalyst in emulsion polymerization, heavy-metal reduction, pharmaceuticals)
3. Formamidinesulfinic acid (fiber bleaching in papermaking, textile bleaching)
4. Zinc formaldehyde sulfoxylate (textile printing and textile bleaching)

All of the abovementioned sulfinic acid derivatives are used in the form of aqueous solutions or dispersions. In aqueous media, sodium dithionite and alkali metal formamidinesulfinate—the free formamidinesulfinic acid is virtually insoluble in water and, in its acid form, has only a very slight reducing action—are only stable for a short time. As a result, even at room temperature they exhibit an excellent reductive capacity and an excellent bleaching effect on fibers. Aqueous preparations of sodium formaldehyde sulfoxylate and of zinc formaldehyde sulfoxylate are stable at room temperature for months. As a result, both formaldehyde sulfoxylates only exhibit their true reducing action at temperatures above 90° Celsius. In strongly alkaline or acidic media or in the presence of suitably strong oxidizing agents, both formaldehyde sulfoxylates do of course also have a reducing effect at temperatures lower than 90° C. This particular property of the formaldehyde sulfoxylates, namely to exhibit a very uniform and easily controlled reducing effect at temperatures between 5° C. and 90° C., is made use of in free-radical-initiated emulsion polymerization. Here, the formaldehyde sulfoxylates are used in various emulsion polymerization systems. In the case of the cold preparation of SBR (styrene butadiene rubber), the polymerization is initiated using organic peroxides. At the low polymerization temperature of about 5° C., the organic peroxides do not, however, decompose into the required free radicals. The peroxide cleavage must be initiated by catalytic amounts of iron(II) salts. The iron in oxidation stage two is converted into oxidation stage three making it no longer suitable for the peroxide cleavage. With the help of the formaldehyde sulfoxylate, the iron(III) ions are again reduced to iron(II) ions—the peroxide cleavage and the free-radical initiation continues. In other emulsion polymerization systems, peroxide compounds, such as hydrogen peroxide or peroxodisulfate, are used as free-radical formers. In order to increase the rate of free-radical formation, reducing agents are again used. Examples which may be mentioned are formaldehyde sulfoxylates, bisulfites, ascorbic acid, isoascorbic acid and sodium erythrobate. Formaldehyde sulfoxylates, in particular sodium formaldehyde sulfoxylate, have proven to be particularly effective and good value reducing agents. During the reduction process, however, the formaldehyde sulfoxylates eliminate formaldehyde. Plastics or polymer dispersions which must not contain formaldehyde are polymerized either using bisulfites, ascorbic acid, isoascorbic acid or sodium erythrobate. Since the formaldehyde-free reducing agents are weaker reducing agents, the disadvantage of less complete polymerization compared with formaldehyde sulfoxylates must be accepted. Furthermore, the use of ascorbic acid, isoascorbic acid and of sodium erythrobate leads to an undesired yellowing of the polymer.

The object of the present invention is to provide novel sulfinic acid derivatives whose chemical properties are as similar as possible to those of formaldehyde sulfoxylate, but which do not eliminate formaldehyde during or after use.

Surprisingly, it has now been found that this object is achieved by sulfinic acid derivatives of the type described in more detail below.

The present invention thus provides sulfinic acid compounds of the formula (I):

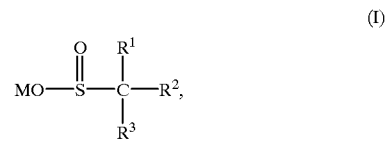

where
- M is a hydrogen atom, an ammonium ion, a monovalent metal ion or an equivalent of a divalent metal ion of the groups Ia, IIa, IIb, IVa or VIIIb of the Periodic Table of the Elements;
- $R^1$ is OH or $NR^4R^5$, where $R^4$ and $R^5$ independently of one another are H or $C_1$–$C_6$-alkyl;
- $R^2$ is H or an alkyl, alkenyl, cycloalkyl or aryl group, it being possible for these groups to have 1, 2 or 3 substituents which are chosen independently of one another from $C_1$–$C_6$-alkyl, OH, O-$C_1$–$C_6$-alkyl, halogen and $CF_3$; and
- R3 is COOM, $SO_3M$, $COR^4$, $CONR^4R^5$ or $COOR^4$, where M, $R^4$ and $R^5$ are as defined above, or, if $R^2$ is aryl, which may be unsubstituted or substituted as defined above, $R^3$ is also H, and the salts thereof.

For the purposes of the present invention, the expressions listed below have the following meanings:

Alkyl represents straight-chain or branched alkyl groups which preferably have 1–6, in particular 1–4, carbon atoms. Examples of alkyl groups are methyl, ethyl, n-propyl, isopropyl, n-butyl, t-butyl, n-hexyl, etc.

The same applies to the alkyl groups in O-alkyl.

Alkenyl represents straight-chain or branched alkenyl groups which preferably have 3–8 carbon atoms, in particular 3–6 carbon atoms. A preferred alkenyl group is the allyl group.

Cycloalkyl is, in particular, $C_3$–$C_6$-cycloalkyl, cyclopentyl and cyclohexyl being particularly preferred.

Aryl (also in aralkyl) is preferably phenyl or naphthyl. If the aryl radical is a phenyl group and is substituted, it preferably has two substituents. These are, in particular, in the 2- and/or 4-position.

Halogen represents F, Cl, Br and I, preferably Cl and Br.

M is preferably an ammonium ion, alkali metal ion or an equivalent of an alkaline earth metal ion or zinc ion. Suitable alkali metal ions are, in particular, sodium and potassium ions. Suitable alkaline earth metal ions are in particular magnesium and calcium ions.

$R^1$ is preferably a hydroxyl or amino group.

$R^2$ is preferably a hydrogen atom or an alkyl or aryl group which may be substituted as above. It preferably has one or two hydroxyl and/or alkoxy substituents.

$R^3$ is preferably either COOM or COOR$^4$ (M and R$^4$ are as defined above) or, if R$^2$ is aryl, which may be substituted as stated above, may also be a hydrogen atom.

A preferred embodiment covers compounds of the formula (I) in which

M is an alkali metal ion or an equivalent of an alkaline earth metal ion or zinc ion;

R$^1$ is a hydroxyl or amino group; R$^2$ is H or alkyl; and

R$^3$ is COOM or COOR$^4$, where M is H, an alkali metal ion or an equivalent of an alkaline earth metal ion, and R$^4$ is C$_1$–C$_6$-alkyl.

A further preferred embodiment covers compounds of the formula (I), in which

M is an alkali metal ion or an equivalent of an alkaline earth metal ion or zinc ion;

R$^1$ is a hydroxyl or amino group;

R$^2$ is an unsubstituted aryl or aryl substituted as stated above, in particular hydroxyphenyl or C$_1$–C$_4$-alkoxyphenyl; and R$_3$ is a hydrogen atom.

The novel compounds are prepared from dithionite salts. Advantageously, a salt having a cation which is also desired in the sulfinic acid compounds is used. The dithionite salts are reacted by preparing those compounds in which R$^2$ is an unsubstituted or substituted aryl radical and R$^3$ is a hydrogen atom, with the corresponding aromatic aldehyde. This reaction can be illustrated using sodium dithionite and 2-hydroxybenzaldehyde as an example by the following reaction equation:

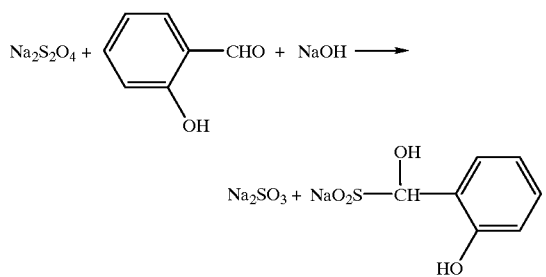

All other compounds of the formula M are prepared by reacting the dithionite salts with the corresponding 1,2-dicarbonyl compound or a sulfonic acid equivalent thereof. The 1,2-dicarbonyl compound used is, in particular, glyoxylic acid or the corresponding keto compounds and their esters. The reaction can be illustrated using sodium dithionite and glyoxylic acid as an example by the reaction equation below:

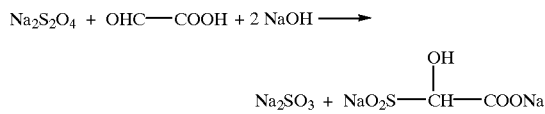

The reaction is generally carried out in an aqueous medium in the presence of a base. The aqueous medium may also include water-soluble organic solvents, such as methanol, ethanol, isopropanol, etc. Bases which may be used are, in particular, alkali metal hydroxides and alkaline earth metal hydroxides. The reaction is generally carried out at ambient temperature; heating of the reaction mixture is generally not required because the reaction is exothermic. The desired product generally precipitates out from the reaction mixture or can be precipitated out by adding polar, water-soluble organic solvents, such as methanol, ethanol, isopropanol, acetone, etc. The resulting product is in the form of the salt which can, if desired, be converted into the free sulfinic acid by acidification or treatment with an acidic ion exchanger.

Furthermore, the product is generally produced in a mixture with the corresponding metal sulfite. In many cases, the mixture also contains the corresponding sulfonic acid and water of crystallization. The novel compounds can be separated off from the accompanying constituents in the usual manner, for example by recrystallization from water or aqueous alcohol.

For use in practice, it is not necessary to separate off the accompanying constituents. On the contrary, it has been found that the action of the novel compounds is even increased by these accompanying constituents. The invention thus also provides the corresponding mixtures with the constituents mention ed. For this purpose, the metal sulfite may be present in an amount up to 40% and the sulfonic acid in an amount up to 60%. The water content may be up to 30%.

The novel compounds are reducing agents whose reducing action is comparable with that of formaldehyde sulfoxylate. However, they have the advantage of not eliminating formaldehyde before, during and after use. The novel compounds are thus preferentially used in those fields where the evolution of formaldehyde is undesired. For example, they can be used as reducing agents in textile printing, in particular in textile discharge printing, in textile bleaching or vat dyeing, or as reducing agents for bleaching minerals, such as kaolin etc., and fibers, for example cellulose fibers. They are preferably used, however, as cocatalyst in emulsion polymerization together with peroxidic initiators in order to allow the polymerization to be carried out at a lower temperature. For this purpose, the sulfinic acids may, if desired, be also used together with oxidizable metal ions, such as Fe$^{2+}$, Mn$^{2+}$ etc. These metal ions are then advantageously used as counterions to the sulfinic acid compounds, i.e. M=Fe$^{2+}$, Mn$^{2+}$ etc.

For use, the novel compounds are generally formulated together with customary additives and auxiliaries. There is no particular limitation in this respect, only that reducing compounds must not be used.

The examples below illustrate the invention without limiting it. The purity figures given in the examples refer to the product which contains water of crystallization which is produced, i.e. the purity is significantly higher when the content of water of crystallization is taken into consideration.

EXAMPLE 1

2-Hydroxyphenylhydroxymethylsulfinic acid, sodium salt

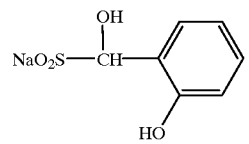

50 ml of 2-hydroxybenzaldehyde and 45 g of 50% strength sodium hydroxide solution were added to an aqueous solution of 90 g of commercially available sodium hydrosulfite (sodium dithionite). After the exothermic reaction had finished, the resulting crude product was separated off using methanol and recrystallized from a methanol/ethanol/water mixture. The 2-hydroxyphenylhydroxymethylsulfinic acid, sodium salt was produced with a purity of 75.8%. The sulfinic acid content was determined using iodometry. The IR spectroscopic data (T=transmission) are as follows:

3551.97 cm$^{-1}$ (28.51 %T); 3175.96 cm$^{-1}$ (19.45 %T); 2915.51 cm$^{-1}$ (29.95 %T); 2747.10 cm$^{-1}$ (34.58 %T); 1899.95 cm$^{-1}$ (61.96 %T); 1682.34 cm$^{-1}$ (44.77 %T); 1641.40 cm$^{-1}$ (38.98 %T); 1594.46 cm$^{-1}$ (32.49 %T); 1505.02 cm$^{-1}$ (42.21 %T); 1455.65 cm$^{-1}$ (17.74 %T); 1387.05 cm$^{-1}$ (27.73 %T); 1330.41 cm$^{-1}$ (40.37 %T); 1280.09 cm$^{-1}$ (30.89 %T): 1244.74 cm$^{-1}$ (23.14 %T) 1200.40 cm$^{-1}$ (31.90 %T); 1155.73 cm$^{-1}$ (30.12 %T) 1111.53 cm$^{-1}$ (29.83 %T); 1098.58 cm$^{-1}$ (32.10 %T); 1072.68 cm$^{-1}$ (28.14 %T); 1030.15 cm$^{-1}$ (16.57 %T); 995.68 cm$^{-1}$ (16.40 %T) 957.46 cm$^{-1}$ (16.83 %T); 872.69 cm$^{-1}$ (43.53 %T); 846.84 cm$^{-1}$ (42.51 %T); 801.62 cm$^{-1}$ (40.51 %T); 762.15 cm$^{-1}$ (28.82 %T); 744.61 cm$^{-1}$ (21.25 %T); 659.92 cm$^{-1}$ (26.13 %T); 629.31 cm$^{-1}$ (30.85 %T); 588.96 cm$^{-1}$ (26.78 %T); 561.45 cm$^{-1}$ (41.13 %T); 496.95 cm$^{-1}$ (30.36 %T).

EXAMPLE 2
4-Methoxyphenylhydroxymethylsulfinic acid, sodium salt

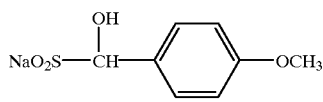

63 g of 4-methoxybenzaldehyde and 45 g of 50% strength aqueous sodium hydroxide solution were added to 90 g of commercially available sodium hydrosulfite in aqueous solution. Evaporation of the resulting solution precipitated out the crude product. The sodium salt of the sulfinic acid was obtained by crystallization from a methanol/ethanol/water mixture having a purity of 68%. The sodium salt of the corresponding sulfonic acid was present as a secondary constituent.

EXAMPLE 3
2-Hydroxy-2-sulfinatoacetic acid, disodium salt

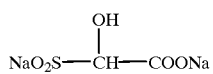

The reaction of 358 g of commercially available sodium hydrosulfite in 800 ml of water with 268 g of 50% strength glyoxylic acid and 285 g of 50% sodium hydroxide solution gave the 2-hydroxy-2-sulfinatoacetic acid, disodium salt in a yield of 95%. The solid crude product contained 43% of sulfinic acid (without water of hydration). Crystallization from a methanol/ethanol/water mixture gave the hydrate of the sulfinic acid in nice crystals. The sulfur-containing constituents were determined using iodometry. The sulfinic acid shows a reaction with indanthrene paper at about 75° C.

The IR spectrum shows the following peaks:

3588.57 cm$^{-1}$ (6.21 %T); 3485.05 cm$^{-1}$ (1.37 %T); 3339.44 cm$^{-1}$ (1.75 %T); 2905.13 cm$^{-1}$ (38.46 %T); 2794.17 cm$^{-1}$ (42.39 %T); 2189.93 cm$^{-1}$ (54.06 %T); 1662.54 cm$^{-1}$ (7.35 %T); 1613.92 cm$^{-1}$ (0.67 %T); 1417.54 cm$^{-1}$ (7.34 %T); 1388.03 cm$^{-1}$ (8.65 %T); 1248.31 cm$^{-1}$ (3.95 %T); 1185.34 cm$^{-1}$ (30.75 %T); 1153.96 cm$^{-1}$ (20.95 %T); 1103.16 cm$^{-1}$ (5.58 %T); 1027.04 cm$^{-1}$ (2.61 %T); 968.33 cm$^{-1}$ (1.77 %T); 938.07 cm$^{-1}$ (26.60 %T); 847.72 cm$^{-1}$ (23.10 %T); 717.14 cm$^{-1}$ (10.46 %T), 645.46 cm$^{-1}$ (14.88 %T); 541.36 cm$^{-1}$ (9.25 %T); 491.77 cm$^{-1}$ (11.95 %T); 445.88 cm$^{-1}$ (19.23 %T).

$^{13}$C nuclear magnetic resonance spectrum (63 MHz): δ(ppm): 93.8 (s); 177.7 (s)

EXAMPLE 4
2-Hydroxy-2-sulfinatoacetic acid, zinc salt

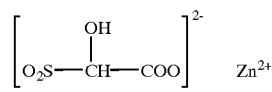

The reaction of 33 g of Zn dust in aqueous medium with sulfur dioxide gave zinc dithionite. This was reacted in situ with 136 g of 50% strength glyoxylic acid.

After the exothermic reaction had finished, 75 g of ZnO were added. The crude product present in the filtrate was precipitated out using methanol and comprised 20% of sulfinic acid and 48% of sulfonic acid (iodometric determination).

EXAMPLE 5
2-Hydroxy-2-sulfinatopropionic acid, disodium salt

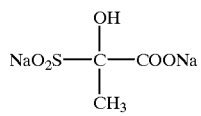

Starting from 89 g of commercially available sodium hydrosulfite in water, the crude product was obtained by reaction with 40 g of pyruvic acid and about 78 g of 50% strength sodium hydroxide solution. The crude product comprised 40% of sulfinic acid and was recrystallized from a methanol/ethanol/water mixture. The content was determined iodometrically. The disodium salt of the corresponding sulfonic acid was present as a secondary constituent.

The IR spectroscopic signals found were as follows:

3484.66 cm$^{-1}$ (6.25 %T); 2995.53 cm$^{-1}$ (26.51 %T); 2758.93 cm$^{-1}$ (32.54 %T); 1592.63 cm$^{-1}$ (0.62 %T); 1456.02 cm$^{-1}$ (16.06 %T); 1436.19 cm$^{-1}$ (17.02 %T); 1397.00 cm$^{-1}$ (4.77 %T); 1367.01 cm$^{-1}$ (7.14 %T), 1190.80 cm$^{-1}$ (2.49 %T), 1038.50 cm$^{-1}$ (0.70 %T);981.07 cm$^{-1}$ (1.42 %T); 943.83 cm$^{-1}$ (7.90 %T); 857.07 cm$^{-1}$ (20.25 %T); 804.64 cm$^{-1}$ (32.86 %T); 790.68 cm$^{-1}$ (34.62 %T);710.08 cm$^{-1}$ (30.79 %T); 659.00 cm$^{-1}$ (11.96 %T); 628.53 cm$^{-1}$ (9.93 %T); 558.19 cm$^{-1}$ (26.14 %T); 522.56 cm$^{-1}$ (16.21 %T); 497.03 cm$^{-1}$ (15.70 %T); 431.34 cm$^{-1}$ (28.83 %T).

EXAMPLE 6
Ethyl 2-hydroxy-2-sulfinatopropionate, sodium salt

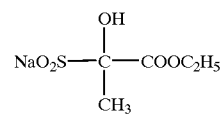

After 90 g of commercially available sodium hydrosulfite in aqueous solution had reacted with 60 g of ethyl pyruvate and 39 g of 50% strength sodium hydroxide solution, the ethyl 2-hydroxy-2-sulfinatopropionate, sodium salt precipitated out during the exothermic reaction as the hydrate. The separated off and dried crude product comprises 79% of sulfinic acid (calculated without water of crystallization). The contents were determined using iodometry. The IR spectroscopic signals can be summarized as follows:

3501.08 cm$^{-1}$ (12.01 %T); 3328.38 cm$^{-1}$ (16.14 %T); 3003.23 cm$^{-1}$ (51.87 %T); 2986.52 cm$^{-1}$ (45.03 %T); 2940.61 cm$^{-1}$ (54.87 %T); 1733.45 cm$^{-1}$ (7.42 %T); 1663.31 cm$^{-1}$ (48.05 %T); 1469.00 cm$^{-1}$ (32.01 %T); 1402.22 cm$^{-1}$ (42.89 %T); 1367.58 cm$^{-1}$ (40.81 %T); 1298.47 cm$^{-1}$ (43.49 %T); 1262.97 cm$^{-1}$ (26.65 %T); 1190.27 cm$^{-1}$ (10.52 %T); 1105.86 cm$^{-1}$ (10.94 %T); 1038.98 cm$^{-1}$ (6.62 %T); 1012.00 cm$^{-1}$ (30.53 %T); 985.42 cm$^{-1}$ (9.37 %T); 948.69 cm$^{-1}$ (28.55 %T); 860.86 cm$^{-1}$ (56.24 %T); 801.55 cm$^{-1}$ (61.53 %T); 685.30 cm$^{-1}$ (51.65 %T); 658.49 cm$^{-1}$ (51.18 %T); 590.17 cm$^{-1}$ (34.18 %T); 523.55 cm$^{-1}$ (34.88 %T): 471.89 cm$^{-1}$ (41.25 %T) 425.61 cm$^{-1}$ (59.75 %T).

EXAMPLE 7

For the textile discharge printing on a black fabric, a printing paste having the following formulation was chosen.

Base formulation of the printing paste:
434 g of water
100 g of potash
6 g of KL 100 thickener (carboxymethylated starch)
40 g of Lameprint IND8 (guar ether+starch ether)
14 g of glycerol
6 g of Printogen (self-emulsifying mineral oil)
600 g of base formulation The formaldehyde-free reducing agent corresponding to Example 3 or sodium formaldehyde sulfoxylate for the comparative mixture were then added to this base formulation.

| Mixture 1 | Comparative mixture |
| --- | --- |
| 600 g of base formulation | 600 g of base formulation |
| 213 g of 2-hydroxy-2-sulfinatoacetic acid, disodium salt corresponding to Example 3 (crude product) | 107 g of sodium formaldehyde sulfoxylate |

The resulting mixtures were then applied to the black fabric next to one another and dried in a drying cabinet. The fabric was then aged at 102° C. for 10 minutes, during which time the dye was reduced. The fabric was thoroughly rinsed to remove residues of thickener and other chemicals, and the undyed fabric became apparent at those places where the reducing agent had previously been applied.

It is evident that the discharge printing has performed well. The rinsing of the preparations presented no problems of any kind. The disodium salt of 2-hydroxy-2-sulfinatoacetic acid can thus be used in textile discharge printing according to current technology. The results of the discharge printing are summarized in Table 1:

TABLE 1

| Whiteness R457 | Mixture 1 | Comparative Mixture |
| --- | --- | --- |
| 1st measurement | 69.55 | 71.40 |
| 2nd measurement | 70.24 | 70.73 |
| 1st yellowness index | 9.83 | 8.91 |
| 2nd yellowness index | 9.51 | 9.05 |

EXAMPLE 8

Bleaching of kaolin

The starting concentration of the kaolin was 250 g/l. The slurry had a pH of 6.5. After the kaolin suspension had been homogenized using a stirrer for 30 minutes, the pH was adjusted to 2.5 using semi-concentrated sulfuric acid.

The disodium salt of 2-hydroxy-2-sulfinatoacetic acid corresponding to Example 3 and sodium formaldehyde sulfoxylate were added as 10% strength solutions and were based on the solids content of the kaolin suspension (see Table 2).

Reaction conditions:

| | |
| --- | --- |
| Temperature: | Room temperature |
| pH: | 2.5 |
| Reaction time: | 2 hours |

TABLE 2

| Kaolin type | Feed amount | Initial whiteness [%] | Final whiteness [%] | Shade | Saturation |
| --- | --- | --- | --- | --- | --- |
| A | [%, absolutely dry] 0.45 of the disodium salt of 2-hydroxy-2-sulfinatoacetic acid corresponding to Example 3 | R 457 73.4 | R 457 76.8 | R 457 1.51 | R 457 0.46 |
| A | 0.3 of sodium formaldehyde sulfoxylate | 73.4 | 74.5 | 1.59 | 0.61 |
| B* | 0.3 of the disodium salt of 2-hydroxy-2-sulfinatoacetic acid corresponding to Example 3 | 79.5 | 82.5 | 1.02 | 0.34 |
| B | 0.3 of sodium formaldehyde sulfoxylate | 79.5 | 79.7 | 1.34 | 0.46 |

Sodium pyrophosphate was added as complexing agent.

The preparation containing the disodium salt of 2-hydroxy-2-sulfinatoacetic acid produces good results in the bleaching of kaolin. The preparation containing the disodium salt of hydroxyacetylsulfinic acid reacted 3–4 times more quickly than the sodium formaldehyde sulfoxylate. The use in the bleaching of minerals, in particular for kaolin, is possible according to current technology.

EXAMPLE 9 (Comparative Example)

400 g of water, 286 g of a 10% strength aqueous solution of Airvol 205 (polyvinyl alcohol, 88% hydrolysed; DP=500; manufactured by Air Products and Chemicals, Inc.), 286 g of a 10% strength aqueous solution of Airvol 107 (polyvinyl alcohol, 98% hydrolysed; DP=500; manufactured by Air Products and Chemicals, Inc.) and 47 g of Igepal CO-887 (non-ionic surfactant, manufactured by Rhone-Poulenc, Inc.; 70% strength aqueous solution of Igepal CO-880 comprises approximately 30 mol of ethylene oxide) were charged to a 3.8 liter pressurized reactor and mixed with 4.8 g of a 1% strength aqueous iron(II) sulfate solution. The reaction mixture was adjusted to a pH of 3.3 using 1.75 g of a 50% strength phosphoric acid solution. 1710 g of vinyl acetate monomer were then metered in. The reaction mixture was stirred at 900 rpm and heated to 35° C. 200 g of gaseous ethylene were then introduced at a pressure up to 20.4 atm. 5.7 g of a 10% strength aqueous solution of isoascorbic acid (pH=4) having the following composition:

270 g of water
30 g of isoascorbic acid 0.8 g of 29% strength ammonium hydroxide solution, were then added. The polymerization was initiated using a total of 10 g of 0.65% strength aqueous hydrogen peroxide solution having the following composition:

589 g of deionized water 11.1 g of 35% strength hydrogen peroxide.

After the polymerization had been initiated, the remaining 295.1 g of the ammonium isoascorbate/isoascorbic acid solution were metered in over the course of 4 hours. The remaining 590.1 g of 0.65% strength hydrogen peroxide solution were added to control the polymerization such that the reaction mixture warmed up from 35° C. to 55° C. over a period of 1 hour and such that the reaction mixture could then be maintained at 55° C. for 3 hours. After a total polymerization time of 4 hours, the content of free vinyl acetate monomer was still 1.5%.

The reaction mixture was cooled to 35° C. and transferred to a pressureless reactor in order to degas excess ethylene. The free vinyl acetate monomer remaining in the emulsion was subsequently polymerized by the addition of 20 g of a 10% strength aqueous isoascorbic acid solution and a 3.5% strength hydrogen peroxide solution and as a result forced down to a final content below 0.5% of free vinyl acetate monomer. The pH of the polymer emulsion was adjusted to the desired pH (see Table 3) using a 14% strength aqueous ammonium hydroxide solution. The physical properties of the polymer emulsion (latex) are summarized in Table 3.

EXAMPLE 10 (Comparative Example)

The emulsion polymerization as in Example 9 was repeated, and in place of the ammonium isoascorbate/isoascorbic acid, an aqueous solution consisting of 270 g of water and 22.1 g of sodium formaldehyde sulfoxylate was used. The results are summarized in Table 3.

EXAMPLE 11 (Cocatalyst in the Emulsion Polymerization)

The emulsion polymerization as in Example 9 was repeated, and in place of the ammonium isoascorbate/isoascorbic acid, an aqueous solution consisting of 270 g of water and 33 g of reducing agent according to Example 3 (crude product) was used. The results are summarized in Table 3.

TABLE 3

| Parameter of the resulting latices | Example 9 (Comparison) slightly yellowish | Example 10 (Comparison) milky white | Example 11 (Invention) milky white |
|---|---|---|---|
| Appearance | | | |
| Solids content [%] | 62.1 | 63.4 | 63.2 |
| pH | 6.5 | 6.0 | 6.2 |
| Viscosity [Pa · s] (60 rpm; 25° C.) | 440 | 380 | 560 |
| Tg (polymer) [° C.] | +5 | +4 | +7 |
| free formaldehyde [ppm] | — | 130 | — |

EXAMPLE 12

Groundwood bleaching

Conditions for the groundwood bleaching:

| | |
|---|---|
| Stock consistency: | 5.4% |
| Bleaching temperature: | 75° C. |
| Bleach addition: | 0.2/0.4/0.6/0.8/1.0% of bleach, absolutely dry (based on dry weight) |
| Bleaching time: | 30 minutes |

For the bleaching, 100 g of groundwood were in each case weighed into polyethylene bags. To add the bleach, aqueous solutions were prepared (1 ml of these solutions comprised 0.2% of each bleach absolutely dry). After the bleach solution had been pipetted in, the bags were immediately tied up, and the contents were thoroughly mixed by kneading the closed bags. The bleaching temperature was regulated using a thermostat (water bath).

After the required bleaching time, the pulp slurry was transferred to measuring flasks and the pH after bleaching was measured. The volume was then made up to 300 ml with tap water and the mixture was homogenized by stirring the pulp slurry. The sheets were formed using a customary suction sheet former using the entire pulp slurry. The resulting sheets were vacuum-dried in the sheet former for 12 minutes.

The whiteness R457 of all of the sheets formed was determined using a whiteness measuring device (Elrepho 2000 from Datacolor). The results are summarized in Table 4.

TABLE 4

| Bleach | Amount of bleach [%, absolutely dry] | Initial pH | Final pH | Whiteness | Whiteness increase[1] |
|---|---|---|---|---|---|
| Sodium formaldehyde sulfoxylate | 0.0 | 6.4 | 6.3 | 65.1 | — |
| | 0.2 | 6.4 | 6.2 | 66.6 | 1.5 |
| | 0.4 | 6.4 | 6.2 | 66.9 | 1.8 |
| | 0.6 | 6.4 | 6.2 | 67.0 | 1.9 |
| | 0.8 | 6.4 | 6.2 | 67.3 | 2.2 |
| | 1.0 | 6.4 | 6.2 | 67.7 | 2.6 |
| Disodium salt of 2-hydroxy-2-sulfinato-acetic acid corresponding to Example 3 | 0.0 | 6.5 | 6.4 | 65.7 | — |
| | 0.2 | 6.5 | 6.4 | 66.7 | 1.0 |
| | 0.4 | 6.5 | 6.5 | 67.2 | 1.5 |
| | 0.6 | 6.5 | 6.6 | 67.6 | 1.9 |
| | 0.8 | 6.5 | 6.6 | 68.0 | 2.3 |
| | 1.0 | 6.5 | 6.7 | 68.1 | 2.4 |

[1]compared with the untreated groundwood

EXAMPLE 13

Deinked pulp bleaching

Conditions for the deinked pulp bleaching:

| | |
|---|---|
| Stock consistency: | 7.4% |
| Bleaching temperature: | 75° C. |
| Bleach addition: | 0.2/0.4/0.6/0.8/1.0% of bleach, absolutely dry |
| Bleaching time: | 60 minutes |

For the bleaching, 70 g of deinked pulp were in each case weighed into polyethylene bags. To add the bleach, aqueous solutions were prepared (1 ml of these solutions comprised 0.2% of each bleach absolutely dry). After the bleach solution had been pipetted in, the bags were immediately tied up, and the contents were thoroughly mixed by kneading the closed bags. The bleaching temperature was regulated using a thermostat (water bath).

After the required bleaching time, the pulp slurry was transferred to measuring flasks and the pH after bleaching was measured. The volume was then made up to 300 ml with tap water and the mixture was homogenized by stirring the pulp slurry. The sheets were formed using a customary suction sheet former using the entire pulp slurry. The resulting sheets were vacuum-dried in the sheet former for 15 minutes.

The whiteness R457 of all of the sheets formed was determined using a whiteness measuring device (Elrepho 2000 from Datacolor). The results are summarized in Table 5.

TABLE 5

| Bleach | Amount of bleach [%, absolutely dry] | Initial pH | Final pH | Whiteness | Whiteness increase[1] |
|---|---|---|---|---|---|
| Sodium | 0.0 | 7.2 | 7.2 | 64.5 | — |
| formalde- | 0.2 | 7.2 | 7.2 | 65.9 | 1.4 |
| hyde | 0.4 | 7.2 | 7.3 | 66.3 | 1.8 |
| sulfoxylate | 0.6 | 7.2 | 7.3 | 66.9 | 2.4 |
|  | 0.8 | 7.2 | 7.3 | 66.9 | 2.4 |
|  | 1.0 | 7.2 | 7.4 | 67.0 | 2.5 |
| Disodium salt of | 0.0 | 7.2 | 7.2 | 64.5 | — |
| 2-hydroxy-2- | 0.2 | 7.2 | 7.4 | 64.9 | 0.4 |
| sulfinato- | 0.4 | 7.2 | 7.4 | 66.0 | 1.5 |
| acetic acid | 0.6 | 7.2 | 7.4 | 66.2 | 1.7 |
| corresponding | 0.8 | 7.2 | 7.5 | 66.5 | 2.0 |
| to Example 3 | 1.0 | 7.2 | 7.5 | 66.3 | 1.8 |

[1]Compared with the untreated deinked pulp

We claim:

1. A sulfinic acid compound of the formula (I)

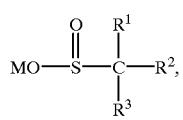

(I)

and the salt thereof, wherein

M is a hydrogen atom, an ammonium ion, a monovalent metal ion or an equivalent of a divalent metal ion of the groups Ia, IIa, IIb, IVa or VIIIb of the Periodic Table of the Elements;

$R^1$ is OH;

$R^2$ is H or an alkyl, alkenyl, cycloalkyl or aryl group, wherein the alkyl, alkenyl, cycloalkyl, and aryl group are unsubstituted or substituted with 1, 2 or 3 substituents which are chosen independently of one another from $C_1$–$C_6$-alkyl, OH, O-$C_1$–$C_6$-alkyl, halogen and $CF_3$; and $R^3$ is COOM or COOR$^4$; and $R^4$ and $R^5$ independently of one another are H or $C_1$–$C_6$ alkyl.

2. The sulfinic acid compound as claimed in claim 1, wherein

M is an ammonium or alkali metal ion or an equivalent of an alkaline earth metal ion or zinc ion.

3. The sulfinic acid compound as claimed in claim 1, wherein $R^2$ is a hydrogen atom or an alkyl or aryl group which are unsubstituted or substituted with one or two hydroxyl or alkoxy substituents.

4. The sulfinic acid compound as claimed in claim 1, wherein $R^3$ is COOM.

5. The sulfinic acid compound as claimed in claim 1, wherein

M is an alkali metal ion or an equivalent of an alkaline earth metal ion or zinc ion; and $R^2$ is H or alkyl.

6. A compound of the formulae:

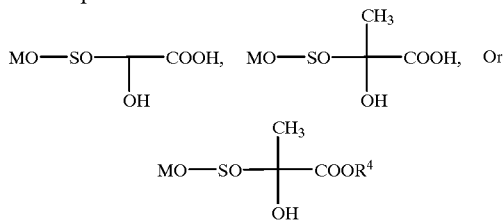

wherein M is Na, K, Mg, Ca, Zn and $R^4$ is $CH_3$ or $C_2H_5$.

7. The mixture of a sulfinic acid compound as claimed in claims 1, 2, 3, 4, or 5 with the sulfonic acid corresponding to the sulfinic acid compound or the salt thereof and with or without the corresponding sulfite.

8. The mixture as claimed in claim 7 having the following composition:

| Compound of the formula (I) | 20–99% by weight |
|---|---|
| Sulfonic acid corresponding to the compound of formula (I) | 0–60% by weight |
| $M_2SO_3$ | 0–40% by weight |

9. The mixture as claimed in claim 8 having the following composition:

| 2-Hydroxy-2-sulfinatoacetic acid, disodium salt: | 40–73% by weight |
|---|---|
| 2-Hydroxy-2-sulfonatoacetic acid, disodium salt: | 2–7% by weight |
| Sodium sulfite: | 0–33% by weight |
| Water: | 5–30% by weight. |

10. The mixture as claimed in claim 8 having the following composition:

| 2-Hydroxy-2-sulfinatoacetic acid, zinc salt: | 20–70% by weight |
|---|---|
| 2-Hydroxy-2-sulfonatoacetic acid, zinc salt: | 5–60% by weight |
| water: | 5–30% by weight. |

11. The mixture as claimed in claim 8 having the following composition:

| 2-Hydroxy-2-sulfinatopropionic acid, disodium salt: | 38–70% by weight |
|---|---|
| 2-Hydroxy-2-sulfonatopropionic acid, disodium salt: | 5–30% by weight |

-continued

| | |
|---|---|
| Sodium sulfite: | 0–33% by weight |
| Water: | 5–30% by weight. |

12. The mixture as claimed in claim 8 having the following composition:

| | |
|---|---|
| Ethyl 2-hydroxy-2-sulfinatopropionate, sodium salt: | 60–80% by weight |
| Ethyl 2-hydroxy-2-sulfonatopropionate, sodium salt: | 0–5% by weight |
| Sodium sulfite: | 0–5% by weight |
| Water | 5–20% by weight. |

13. A method of reducing a chemical compound, the method comprising contacting the compound with a sulfinic acid compound according to claims 1, 2, 3, 4, 5 or 6 under conditions that permit reduction.

14. The method according to claim 14, wherein the sulfinic acid compound is a cocatalyst in emulsion polymerization or redox catalyst system in plastics production.

15. The method according to claim 14, wherein the sulfinic acid compound is a reducing agent component for textile printing, in textile bleaching or vat dyeing or a reducing bleach for mineral refining or fiber finishing.

\* \* \* \* \*

UNITED STATES PATENT AND TRADEMARK OFFICE
CERTIFICATE OF CORRECTION

PATENT NO.   : 6,211,400 B1
DATED        : April 3, 2001
INVENTOR(S)  : Josef Berghofer and Harry Rothmann It is certified that error appears in the above-identified patent and that said Letters Patent is hereby corrected as shown below:

<u>Column 11, claim 1,</u>
Line 62, delete "and $R^5$ independently of one another are" and insert therefor -- is --.

Signed and Sealed this

Second Day of April, 2002

Attest:

JAMES E. ROGAN
Attesting Officer
Director of the United States Patent and Trademark Office

(12) EX PARTE REEXAMINATION CERTIFICATE (9034th)
United States Patent
Berghofer et al.

(10) Number: US 6,211,400 C1
(45) Certificate Issued: May 29, 2012

(54) SULPHINIC ACID DERIVATIVES, METHOD FOR PRODUCING THEM, AND THEIR USE

(75) Inventors: Josef Berghofer, Heilbronn (DE); Harry Rothmann, Daisbach (DE)

(73) Assignee: L. Bruggemann KG, Heilbronn (DE)

Reexamination Request:
No. 90/009,828, Sep. 29, 2010

Reexamination Certificate for:
Patent No.: 6,211,400
Issued: Apr. 3, 2001
Appl. No.: 09/319,108
Filed: May 27, 1999

Certificate of Correction issued Apr. 2, 2002.

(22) PCT Filed: Jul. 1, 1998

(86) PCT No.: PCT/EP98/04055
§ 371 (c)(1),
(2), (4) Date: May 27, 1999

(87) PCT Pub. No.: WO99/18067
PCT Pub. Date: Apr. 15, 1999

(30) Foreign Application Priority Data
Oct. 2, 1997 (DE) .......................................... 197 43 759

(51) Int. Cl.
C07C 313/02 (2006.01)
C07C 313/04 (2006.01)
C07C 313/00 (2006.01)
C08F 2/22 (2006.01)
C08F 4/40 (2006.01)
C08F 4/00 (2006.01)
C11D 3/00 (2006.01)
C11D 3/34 (2006.01)
D06P 1/22 (2006.01)
D06P 5/13 (2006.01)
D06P 1/62 (2006.01)
D06P 1/44 (2006.01)
D06P 1/00 (2006.01)
D06P 5/15 (2006.01)
D21C 9/10 (2006.01)
D06L 3/10 (2006.01)

(52) U.S. Cl. .......................................... 560/150; 562/125
(58) Field of Classification Search ........................ None
See application file for complete search history.

(56) References Cited

To view the complete listing of prior art documents cited during the proceeding for Reexamination Control Number 90/009,828, please refer to the USPTO's public Patent Application Information Retrieval (PAIR) system under the Display References tab.

*Primary Examiner* — Ling Xu

(57) ABSTRACT

The present invention relates to sulfinic acid compounds of the formula (I)

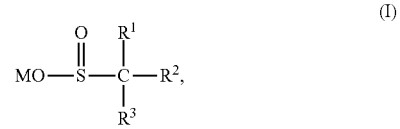

where the substituents are as defined in the description.

The novel sulfinic acid compounds can be used as reducing agents which do not eliminate formaldehyde.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 3, 5-6, 9-10 and 14-15 are determined to be patentable as amended.

Claims 2, 4, 7-8 and 11-13, dependent on an amended claim, are determined to be patentable.

New claims 16-29 are added and determined to be patentable.

1. A sulfinic acid compound of the formula (I)

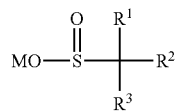

and the salt thereof, wherein

M is a hydrogen atom, an ammonium ion, a monovalent metal ion or an equivalent of a divalent metal ion of the groups Ia, IIa, IIb, IVa or VIIIb of the Periodic Table of the Elements;

$R^1$ is OH;

$R^2$ is [H or] an alkl, alkenyl, cycloalkyl or aryl group, wherein the alkyl, alkenyl, cycloalkyl, and aryl group are unsubstituted or substituted with 1, 2 or 3 substituents which are chosen independently of one another from $C_1$-$C_6$-alkyl, OH, O-$C_1$-$C_6$-alkyl, halogen and $CF_3$; and $R^3$ is COOM or $COOR^4$; and $R^4$ is H or $C_1$-$C_6$ alkyl.

3. The sulfinic acid compound as claimed in claim 1, wherein $R^2$ is [a hydrogen atom or] an alkyl or aryl group which are unsubstituted or substituted with one or two hydroxyl or alkoxy substituents.

5. The sulfinic acid compound as claimed in claim 1, wherein

M is an alkali metal ion or an equivalent of an alkaline earth metal ion or zinc ion; and $R^2$ is [H or] alkyl.

6. A compound of the formulae:

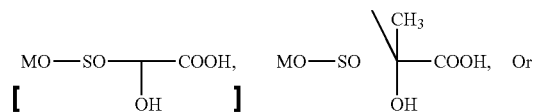

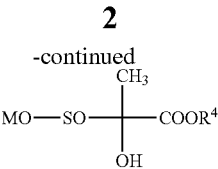

wherein M is Na, K, Mg, Ca, Zn and $R^4$ is $Ch_3$ or $C_2H_5$.

9. The mixture as claimed in claim 8 having the following composition:

| | |
|---|---|
| [2-Hydroxy-2-sulfinatoacetic acid] Compound of the formula (I), disodium salt: | 40-73% by weight |
| [2-Hydroxy-2-sulfonatoacetic acid] Sulfonic acid corresponding to the compound of formula (I), disodium salt: | 2-7% by weight |
| Sodium sulfite: | 0-33% by weight |
| Water: | 5-30% by weight. |

10. The mixture as claimed in claim 8 having the following composition:

| | |
|---|---|
| [2-Hydroxy-2-sulfinatoacetic acid] Compound of the formula (I), zinc salt: | 20-70% by weight |
| [2-Hydroxy-2-sulfonatoacetic acid] Sulfonic acid corresponding to the compound of formula (I), zinc salt: | 5-60% by weight |
| water: | 5-30% by weight. |

14. The method according to claim [14] *13*, wherein the sulfinic acid compound is a cocatalyst in emulsion polymerization or redox catalyst system in plastics production.

15. The method according to claim [14] *13*, wherein the sulfinic acid compound is a reducing agent component for textile printing, in textile bleaching or vat dyeing or a reducing bleach for mineral refining or fiber finishing.

*16. A composition comprising a sulfinic acid compound of formula (II):*

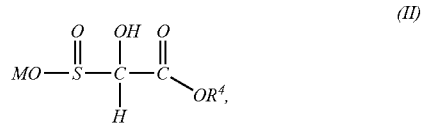

*wherein:*

$R^4$ *is M, H or $C_1$-$C_6$ alkyl;*

*M is an ammonium ion, a monovalent metal ion or an equivalent of a divalent metal ion of group Ia, IIa, IVa or VIIIb according to the Periodic Table of the Elements; and*

*said composition is free of metal ions other than M.*

*17. The composition of claim 16, wherein $R^4$ is H.*

*18. The composition of claim 17, wherein M is an alkaline metal ion.*

*19. The composition of claim 18, wherein M is $Na^+$.*

*20. The composition of claim 16, wherein $R^4$ is M.*

*21. The composition of claim 20, wherein M is an alkaline metal ion.*

*22. The composition of claim 21, wherein M is $Na^+$.*

*23. A mixture of the sulfinic acid compound of formula (II) with the sulfonic acid compound of formula (III), or the salts* thereof, and with or without the corresponding metal sulfite, having the following composition:

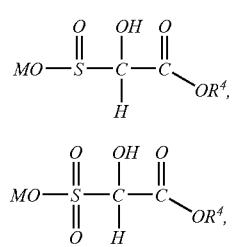

| | |
|---|---|
| Sulfinic acid compound of formula (II): | 20-99% by weight |
| Sulfonic acid compound of formula (III): | 0-60% by weight |
| $M_2SO_3$: | 0-40% by weight | wherein:

$R^4$ is M, H or $C_1$-$C_6$ alkyl;

M is an alkaline metal ion or an equivalent of alkaline earth metal ion; and said mixture is free of metal ions other than M.

24. The mixture of claim 23, having the following composition:

| | |
|---|---|
| 2-Hydroxy-2-sulfinatoacetic acid, disodium salt: | 20-99% by weight |
| 2-Hydroxy-2-sulfonatoacetic acid, disodium salt: | 0-60% by weight |
| $Na_2SO_3$: | 0-40% by weight |

25. The mixture of claim 24, having the following composition:

| | |
|---|---|
| 2-Hydroxy-2-sulfinatoacetic acid, disodium salt: | 40-73% by weight |
| 2-Hydroxy-2-sulfonatoacetic acid, disodium salt: | 2-7% by weight |
| $Na_2SO_3$: | 5-30 40% by weight |
| Water: | 5-30% by weight. |

26. A mixture having the following composition:

| | |
|---|---|
| 2-Hydroxy-2-sulfinatoacetic acid, zinc salt: | 20-70% by weight |
| 2-Hydroxy-2-sulfonatoacetic acid, zinc salt: | 5-60% by weight |
| Water: | 5-30% by weight |

27. A method of reducing a chemical compound, the method comprising contacting the compound with a composition of claim 16 or a mixture of claim 23 or 26 under conditions that permit reduction.

28. The method according to claim 27, wherein said composition or said mixture is used as a cocatalyst in emulsion polymerization or redox catalyst system in production of plastics.

29. The method according to claim 27, wherein said composition or said mixture is used as a reducing agent component for textile printing, textile bleaching or vat dyeing, or as a reducing bleach for mineral refining or fiber finishing.

* * * * *